United States Patent [19]

Marwil

[11] 4,097,339

[45] Jun. 27, 1978

[54] FERMENTATION APPARATUS

[75] Inventor: Stanley J. Marwil, Bartlesville, Okla.

[73] Assignee: Phillips Petroleum Company, Bartlesville, Okla.

[21] Appl. No.: 742,817

[22] Filed: Nov. 18, 1976

[51] Int. Cl.² .............................................. C12B 1/00
[52] U.S. Cl. ................................... 195/142; 195/139; 195/143
[58] Field of Search ............... 195/142, 143, 115, 107, 195/108, 109, 139

[56] References Cited

U.S. PATENT DOCUMENTS

| | | | |
|---|---|---|---|
| 2,983,652 | 5/1961 | Baerfuss et al. | 195/143 |
| 3,114,677 | 12/1963 | Stich | 195/142 |
| 3,575,813 | 4/1971 | Rothmayr | 195/139 |
| 3,616,260 | 10/1971 | Muller | 195/107 |
| 3,622,465 | 11/1971 | Orgel et al. | 195/96 |
| 3,681,200 | 8/1972 | Ridgway | 195/142 |
| 3,824,151 | 7/1974 | Iijima et al. | 195/109 X |
| 3,844,893 | 10/1974 | Hitzman | 195/115 |
| 3,962,042 | 6/1976 | Malick | 195/143 |

OTHER PUBLICATIONS

Muller, "Methane Gas Fermentation Technology," Process Biochemistry, Jun. 1972, pp. 37–39.

Primary Examiner—R. B. Penland

[57] ABSTRACT

A fermentation apparatus comprising a fermentation section; and a contiguous upper absorber section comprising a gas-contacting zone, gas-venting means, liquid knock-out zone, means adapted to receive recycle lean fermentation liquor, means adapted to receive makeup water and nutrients, and means to pass gaseous effluent from the fermentation section through the absorber section.

10 Claims, 1 Drawing Figure

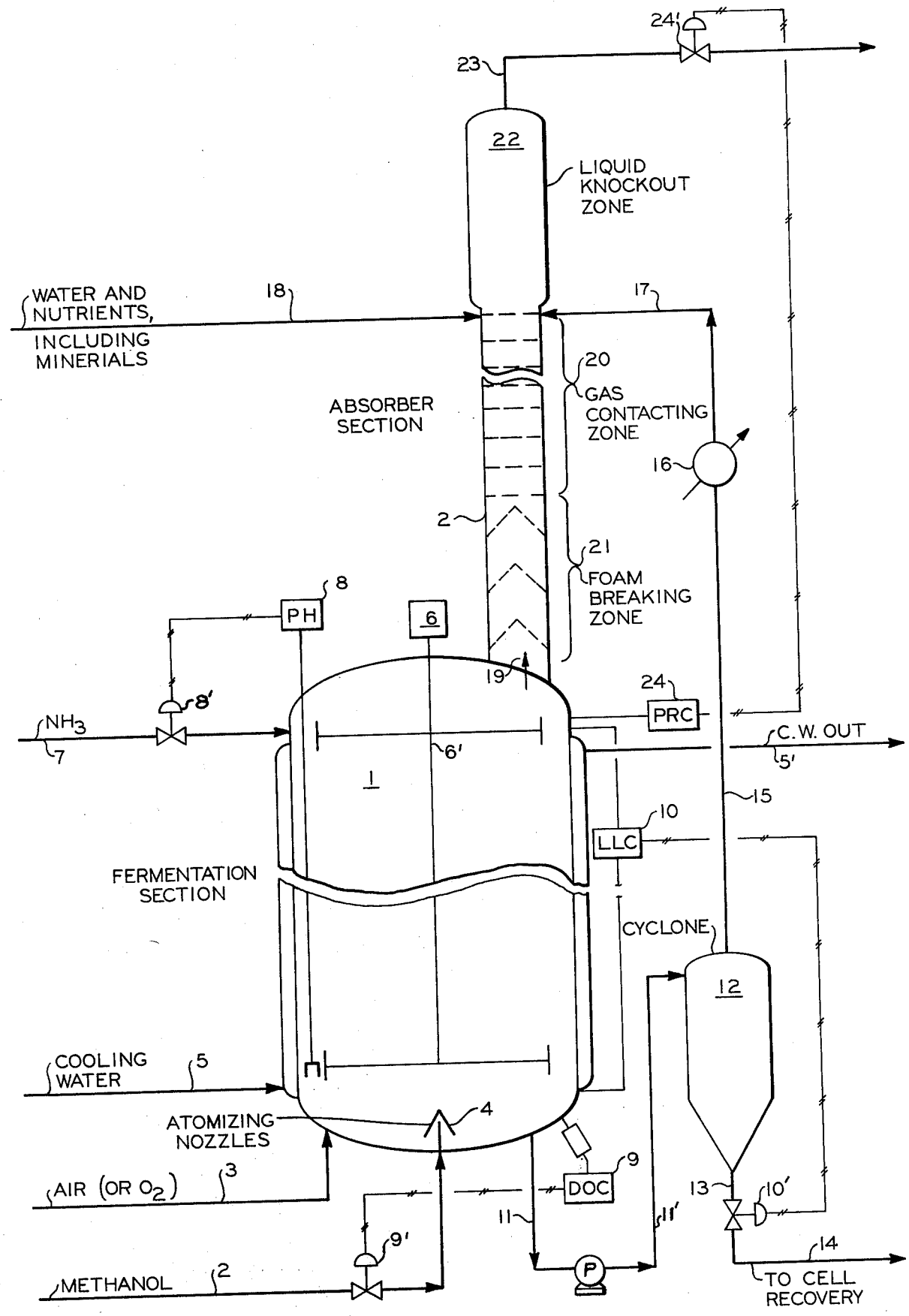

FERMENTATION APPARATUS

FIELD OF THE INVENTION

The invention relates to apparatus for fermentation with microorganisms under aerobic fermentation conditions.

BACKGROUND OF THE INVENTION

Efforts to relieve the worldwide shortages of protein have included various biosynthesis processes. Biologically produced single cell protein (SCP) has been obtained by the growth of a variety of microorganisms including bacteria, yeast and fungi on a variety of carbon-containing substrates. Petroleum hydrocarbons have been employed as a carbon and energy source, but have faced practical difficulties in the lack of water solubility, and in the high consumption of oxygen to assist in the microbial conversion. Other processes have centered on the use of oxygenated hydrocarbon derivatives as feedstocks due to the inherent water solubility of such feedstocks, and hence the ease of handling since microbial conversion processes are essentially conducted under aqueous conditions.

Aerobic microbial conversions are highly exothermic oxidation reactions which demand large quantities of molecular oxygen, and which produce large quantities of heat. The heat must be removed continuously and consistently, or risk overheating of the system and death of the microorganisms, or at least severe limitations on growth of the microorganisms as temperatures rise, and hence severe reductions in efficiencies. Consistant constant supplies of molecular oxygen are necessary to maintain high fermentation efficiencies, and at the same time to assist in providing good heat transfer.

To maintain high fermentation efficiencies in commercial fermentations, oxygen is supplied as a molecular oxygen-containing gas free of any stray microorganisms into the culture media under conditions to provide maximum contact of the oxygen with the culture media so as to dissolve as much oxygen into the aqueous media as possible, as well as to assist in providing heat transfer.

High oxygen transfer rates have been achieved heretofore by conducting a fermentation process as a foam-type process to assist in achieving a high surface area for contact between the liquid phase and the gas phase, in order to obtain a high rate of oxygen transfer from the gas phase into the aqueous phase, and at the same time to assist in obtaining a good rate of removal of carbon dioxide, a natural consequence of aerobic fermentation processes, and heat from the aqueous medium to the gas phase which then is exhausted for such use as may be suitable.

There is a continuing need for improved apparatus suitable for conducting aerobic fermentation processes with high oxygen transfer rates and to provide effective contact between the aqueous medium and the oxygen-containing gas phase, and at the same time, provide an apparatus which is basically straightforward in construction, economical to manufacture and maintain, and yet well adapted for its intended use.

BRIEF DESCRIPTION OF THE DRAWING

In accordance with my invention, my fermentation apparatus comprises a fermentation section 1 with a contiguous upper absorber section 2. The contiguous upper absorber section 2 comprises a foam-breaking zone 21, a gas-contacting zone 20, a liquid knock-out zone 22, means adapted to receive recycle lean fermentation liquor 17, means to receive makeup water and nutrients 18, means to receive gaseous effluent 19 from the fermentation section 1, and gas-venting means 23.

Rich culture media, rich in single cell protein (SCP), is removed 11 continuously from the fermentation section 1. The cellular SCP materials are separated 12, and the lean ferment 15 fed back 17 to the absorber section 2 through the gas-containing zone 20 of the aborber section 2. In the absorber section 2, this return liquid stream 17 of lean ferment is contacted with exhaust gases 19 leaving the fermentation section 1, thus enriching the return (recycle) lean stream in oxygen, since the exhaust gases 19 are still relatively high in unconsumed oxygen. Makeup water and nutrients, including minerals, also are fed 18 into the system through the gas-contacting zone 20 of the absorber section 2, so that these, too, become enriched in oxygen prior to actually entering the fermentation section 1.

DETAILED DESCRIPTION OF THE INVENTION

My fermentation apparatus comprises a fermentation section 1 with an upper contiguous sieve tray absorber section 2. The drawing, designed to assist one skilled in the art, illustrates the general overall apparatus including feed streams and controls suitable for employing the fermentation apparatus in an aerobic fermentation process.

The fermentation section 1 receives a feed of a carbon and energy source, such as an oxygenated hydrocarbon having 1 to 30 carbon atoms, preferably an oxygenated hydrocarbon having such as 1 to 10 carbon atoms, more preferably a lower alcohol, such as methanol 2, molecular oxygen source 3, which can be air, enriched air, or substantially pure oxygen, or combination, usually feeding via nozzles 4, such as atomizing nozzles, into the lower area of the fermentor section 1. Such molecular oxygen source 3 and carbon and energy source 2 are shown fed separately, but optionally can be fed together, if desired, through a single input line (not shown). The fermentation section 1 preferably is supplied with cooling water 5 feeding cooling water into and out of 5' cooling means such as a jacket system as shown, or into an internal coil cooling system means (not shown), if desired, or both. The fermentation section 1 preferably is equipped with motor driven 6 stirring means 6' so as to maintain effectively continuous flux of the aqueous ferment in the fermentation section 1 of the fermentation apparatus. The fermentation section 1 has means 7 for feeding a nitrogen source, such as ammonia, ammonium hydroxide, or the like, which can be fed manually (not shown), or can be controlled as shown by means of a pH sensor controller 8 which monitors the pH of the aqueous fermentation liquor in the fermentation section 1, produces a signal in response thereto, to control the rate of input of ammonia as needed. The input of carbon and energy source such as methanol 2 can be controlled manually, fed continuously, or can be controlled as shown more precisely by a dissolved oxygen controller 9 monitoring on the fermentation section liquor, if desired. Such a dissolved oxygen controller DOC 9 monitors the dissolved oxygen level of the aqueous fermentation liquor in the fermentation section 1, produces a signal responsive thereto, which can be used as shown to control 9' the input of the carbon and energy source material to avoid overfeeding thereof. The DOC 9 probe, if desired, optionally can be in line 11 discharge from the fermentation section.

The fermentation section 1 is equipped with means 11 to remove aqueous ferment, preferably continuously, from the fermentation section 1. The aqueous ferment stream 11 is a mixture of single cell protein, water, nutrients, including minerals, and the like, which then is separated 12, such as in a cyclone 12 as shown, into a stream of rich liquid 13 containing substantially all of the cells, and a stream of lean spent ferment 15 for recycle as separated medium. The stream 13 containing the cells is removed and sent to cell recovery 14 for further processing and treatment.

The cell-rich stream 13 rate of discharge can be controlled manually (not shown), or, and preferably, liquid level controller 10 (LLC) monitors the liquid level in the fermentation section 1, produces a signal in response thereto, and discharges 10' the cell-rich stream 14 at suitable rate to maintain desired level in the fermentation section 1.

The separated lean aqueous liquor 15, cooled if desired 16, is returned 17 to the absorber section 2 of the fermentation apparatus. The return of the spent separated medium 17 is to the gas-contacting zone 20 of the absorber section 2. This gas-contacting zone 20 also is designed to receive stream 18 which supplies water and nutrients, including minerals.

The absorber section is connected with the fermentation section by means so as to receive exhaust or off-gases 19 from the fermentation section 1. The exhaust or off-gases 19 comprise a gaseous phase augmented in carbon dioxide, and depleted to some extent of oxygen, as compared to the input air stream 3. However, this exhaust off-gas stream 19 nevertheless contains large proportions of oxygen desirable to be used at least to some extent if at all possible.

The absorber section preferably is equipped in its lower area with a foam-breaking zone 21 so as to avoid entrainment of excessive quantities of foam from the fermentation section 1, since aerobic fermentation reactions generally operate with a substantial foam level, since foam provides very large total surface areas of contact between aqueous ferment and input oxygen, thus assisting oxygen absorption, and heat removal.

In the absorber section 2, the exhaust gases 19 from the fermentation section 2 are intimately contacted in the gas-contacting zone 20 with lean recycle spent media 17, as well as intimately contacted with incoming water and nutrients 18, including minerals. The result is that the recycle stream 17 and the incoming makeup water and nutrients stream 18 intimately admix 20 in contact with oxygen-laden off-gases 19 to form a combined stream augmented or enriched in molecular oxygen, which then feeds downwardly through the absorber section into the fermentation section 1. The combined recycle stream and the fresh nutrients and the water stream also are at least slightly warmed, to avoid cold shock to the microorganisms. The contacting method and apparatus also aid heat removal from the system.

The upper area of the absorber section 2 provides a liquid knock-out zone 22 so that any entrained moisture in the now further-depleted-of-oxygen exhaust gases can be removed. The exhaust gases are removed 23 for final exhaust. The rate of discharge of the vented gases can be on an as produced basis, or, as shown, a pressure relief control 24 PRC preferably is employed to monitor pressure in the fermentor section 1, produce a signal in response thereto, and discharge vent gases accordingly. This controlled vent gas release also permits operation of the ferment in the fermentation section under greater than atmospheric pressure, which frequently is desirable in aerobic fermentations to thus increase the solubility of molecular oxygen in the aqueous ferment.

Typically, a 10,000 liter fermentation section operated at about 45° C under 2 atmospheres pressure would receive a feed of about 500 liters per hour of methanol and about 20,000 liters per hour of air. Water and nutrients, excluding the recycle stream, would be fed at a liquid rate of about 2,000 to 5,000 liters per hour through the absorber section. From the lower area of the fermentation section would be withdrawn about 40,000 liters per hour of ferment containing 20 to 40 grams of cells per liter, subjected to separation to produce a cellular stream containing about 100–120 grams of cells per liter as a concentrated cellular stream, and the remainder of the cell-depleted recycle ferment stream then is recycled to the absorber section. The gas stream 19 leaving the fermentation section 1 would be estimated to contain on the order of about 19 plus mol percent oxygen, and the depleted stream 23 leaving the absorber section would contain such as about 18 mol percent oxygen. While these relationships would presently be considered the best relationships for the fermentor size involved, nevertheless other relationships would be suitable and effective depending on the specific microorganism involved, specifically desired fermentation temperature, pressure involved which could be higher or lower, and the like.

My fermentation apparatus comprising the fermentation section and the absorber section can be constructed of any suitable material of construction, such as glass, or the like, though generally considering the pressures involved, and the need to maintain clean conditions because of the ultimate food-use of the single cell protein, stainless steel such as 304 or 316 and preferably should be employed.

The absorber section comprises a basically three-zone apparatus, includes a liquid knock-out zone, a foam-breaking zone comprising, e.g., mechanical means such as a packing of continuous metal shavings or a multiple 60° perforated cone baffles, ultrasonic means, or other means known in the art for breaking foam, and a gas-contacting zone, which comprises the zone above the foam-breaking zone and below the liquid knock-out zone and the input points for the water and nutrient stream and the recycle stream.

The upper zone, the liquid knock-out zone, preferably should be an unpacked zone of sufficient diameter so as to provide at least about a 50 percent reduction in linear gas velocity, e.g., a diameter of about $\frac{1}{4}$ to $\frac{1}{2}$ greater than that of the other zones of the absorber section. The height can vary considerably and does not appear critical so long as it is suitable for liquid knock-out.

The gas-contacting zone comprises a series of perforated trays, one above another in parallel fashion, each tray typically having such as about 40 percent free area as represented by the perforations. The size and number of holes will depend in part on the liquid and gas rates through the gas-contacting zone and can be readily calculated by one skilled in the art of sieve tray design. Typically, the foam-breaking zone is of the same diameter as the gas-contacting zone, and its length or height can vary considerably as long as it is sufficient to effectively break foam from the fermentation section. Any suitable foam-breaking zone configuration can be employed. One presently considered particularly suitable packing comprises a spaced series of perforated cones of about a 60° angle.

The fermentation section generally will be of a relatively fat cylindrical shape. The gas-contacting zone comparatively will be of a long slim cylindrical shape. The fermentation section preferably should have about a 2:1 to 6:1, more preferably a 2.5:1 to 4.5:1, length::diameter ratio. Typically, the fermentation section preferably should have a height similar to that of the gas-containing zone. The gas-contacting zone of the absorber section preferably should have a 12:1 to 24:1, more preferably a 14:1 to 20:1, length:diameter ratio.

In general, the ratio of the fermentation section height to the gas-contacting zone height perferably should be within the range of about 0.6:1 to 1.5:1, more preferably about 0.7:1 to about 1.2:1. Typically the fermentation section preferably should have a diameter of about 3 to 8, more preferably 4 to 6, times the diameter of the gas-contacting and foam-breaking zone.

A typical fermentation section would be such as about 5 feet in diameter by about 16 feet high. A typical gas-contacting zone for use with such a fermentation section would be about 1 foot in diameter by about 16 feet high. The trays in the gas-contacting zone of such an absorber section would be set about 1 foot apart. Typically, the foam-breaking zone and the liquid knock-out zone would be each about 2½ to 3 feet long.

In the apparatus in accordance with my invention, the carbon and energy source material or substrate for the fermentation process employing my apparatus preferably is a carbon-oxygen-hydrogen-containing water-soluble compound or compounds. The term "oxygenated hydrocarbon" is intended to be a generic term descriptive of the compounds employable, and not necessarily a limiting term referring to the source of the substrate. Thus, the oxygenated hydrocarbons can include alcohols, ketones, esters, ethers, acids, and aldehydes, which are substantially water-soluble in character, and should be limited, because of this characteristic, to up to about 10 carbon atoms per molecule, recognizing some variation in this value depending on the basic chemical character of the substrate. Certainly, mixed substrates primarily of alcohols, but which contain minor amounts of other oxygenated hydrocarbons, are expected to be widely commercially available and to be suitable.

Illustrative examples of the substrates include the presently preferred methanol and ethanol, most preferably methanol because of availability and low relative cost, as well as 1-propanol, 1-butanol, 1-pentanol, 1-hexanol, 1,7-heptanediol, 2-heptanol, 4-methyl-2-pentanol, pentanoic acid, 2-methylbutanoic acid, 2-pentanol, 3-methyl-1-butanol, 3-methyl-2-butanol, 2-butanol, 2-methyl-1-propanol, 2-methyl-2-propanol, 2-propanol, formic acid, acetic acid, propanoic acid, methyl formate, ethyl formate, ethyl acetate, formaldehyde, acetaldehyde, propanal, butanal, 2-methylpropanal, butanoic acid, 2-methylpropanoic acid, pentanoic acid, glutaric acid, hexanoic acid, 2-methylpentanoic acid, heptanedioic acid, decanedioic acid, heptanoic acid, 4-heptanone, 2-heptanone, octanoic acid, 2-ethylhexanoic acid, glycerine, ethylene glycol, propylene glycol, 2-propanone, 2-butanone, diethyl ether, methyl ethyl ether, dimethyl ether, dipropyl ether, propyl isopropyl ether, and the like, including various mixtures.

A presently preferred ground of such carbon and energy source materials are the water-soluble aliphatic monohydric alcohols. Due to the water solubility, of these most preferred are the lower alcohols of 1 to 4 carbon atoms per molecule for commercial availability, and still more preferred are ethanol and methanol, presently with methanol being most preferred, due to the low relative cost of these feedstocks.

It is feasible to employ mixtures of any of these oxygenated hydrocarbons if desired or convenient. Petroleum gases, typically, can be subjected to oxidation procedures and the resulant admixture employed, such as natural gas and the like which by oxidation provide mixtures predominantly of the corresponding alcohol, though with minor components of various ketones, aldehydes, ethers, acids, and the like.

Where the carbon feed source material contains undesirable quantities of aldehydes, which could be deleterious to the microorganisms employed for fermentation, the microbial feed to the fermentor preferably is priorly contacted with a nitrogen-containing compound reactive with the aldehydes and effective to negate the otherwise deleterious effects.

Suitable for this purpose are nitrogen-containing compounds such as ammonia or of ammonia type such as ammonium hydroxide, ammonium sulfate, ammonium nitrate, ammonium phosphate, and the like, using about 0.01 to 10 mol equivalents of such a nitrogen-containing compound per mol of aldehyde.

Culturing is accomplished in a growth medium comprising an aqueous mineral salt medium, the carbon and energy source material, molecular oxygen, a source of nitrogen, and, of course, a starting innoculum of the particular species of microorganism to be employed. Any microorganisms which can grow on the oxygenated hydrocarbon substrate can be employed, with the innoculum thereof preferably added at the time of start-up.

The particular microorganism employed in my apparatus does not appear critical. Among the microorganisms suitable for the types of fermentation described are the bacteria, yeasts, and fungi, such as from the following genera:

Bacteria: Bacillus, Pseudomonas, Protaminobacter, Micrococcus, Arthrobacter, Corynebacterium, Methanomonas, Methylococcus, Methylomonas, Methylobacter, Methylosinus, Methylocystis, Curtobacterium, Acinebacter, Brevibacterium, Nocardia, Mycobacterium, Streptomyces, and Actinomyces.

Yeasts: Candida, Hansenula, Torulopsis, Pichia, Saccharomyces, Rhodotorula, Brettanomyces, and Debaryomyces.

Fungi: Aspergillus, Monilia, Rhizopus, Penicillium, Fusarium, Mucor, Alternaria, Hyphomicrobium, and Helminthosporium.

Exemplary of suitable microorganisms are *Pseudomonas methanica*, which has been assigned the numerical designation NRRL B-3449 by the United States Department of Agriculture, Agricultural Research Service, Northern Regional Research Laboratories of Peoria, Illinois; *Pseudomonas fluorescens*, numerical designation NRRL B-3452; *Methanomonas methanica, numerical designation NRRL B-3450; Methanomonas methanooxidans*, numerical designation NRRL B-3451; *Arthrobacter parafficum*, numerical designation NRRL B-3453; *Corynebacterium simplex*, numerical designation NRRL B-3454; *Bacillus sp.*, numerical designation NRRL B-8065; and *Bacillus sp.*, numerical designation NRRL B-8066. Combinations of microorganisms also can be employed.

Molecular oxygen conveniently is supplied to the fermentation media or broth as a molecular oxygen-containing gas such as air at atmospheric or elevated pressure, or an oxygen-enriched air, or even a substantially pure oxygen stream, where such are convenient and available. In effect, using an oxygenated hydrocarbon substrate means that a part of the oxygen needed for growth of the microorganism already is supplied by the oxygen content of the substrate itself. Nevertheless, additional quantities of molecular oxygen must be supplied for growth since the assimilation of the substrate and the corresponding growth of the microorganism is, in effect, a combustion process.

In general, between about 0.1 and 10, preferably about 0.7 to 2.5, volumes per minute of air of normal oxygen content are supplied to the reactor per volume of liquid in the fermentation section.

The pressure employed for the microbiological conversion process can range widely, and pressures of about 0.1 to 100 atmospheres, more usually 1 to 30 atmospheres, and presently preferably definitely over atmospheric pressure such as about 2 atmospheres of pressure, are employed. Greater than atmospheric pressures certainly are advantageous in that such pressures tend to increase the dissolved oxygen concentration of the aqueous fermentation admixture, which in turn tends to increase cellular growth rates. Higher than atmospheric pressures certainly are preferred as fermentation temperatures increase, since oxygen solubilities tend to decrease at the elevated temperatures, and increased pressure helps to compensate for this. Foam-filled fermentation section means tend to assist oxygen transfer necessary for high cell densities and rapid growth rates. My apparatus is particularly unique, since it helps to achieve maximum oxygen intake by passing the oxygen-containing gas upwardly through the fermentation broth, and further by passing the exhaust gases from the fermentation section upwardly through the incoming aqueous nutrient medium, thus getting as much oxygen into the system as possible, while utilizing minimum inputs of total air, thus minimizing total costs.

Nutrients such as minerals and a source of assimilable nitrogen, in addition to the oxygen and carbon and energy sources as described, are needed. The source of nitrogen can be any nitrogen-containing compound capable of providing nitrogen in a form suitable for metabolic utilization by the microorganism. Various organic nitrogen source compounds can be utilized such as other proteins, urea, or the like, but most usually inorganic nitrogen source materials are more economical and practical, most particularly ammonia and ammonium compounds, and of these conveniently ammonia or ammonium hydroxide.

The pH range in the aqueous microbial fermentation admixtures should be in the exemplary range of about 5 to 9, though operation with particular species below or above this is possible. The pH preferences in the fermentation depend to some extent not only on the microorganism, but also on the particular medium and mineral balance employed.

In addition to the oxygen, the nitrogen, and carbon and energy sources, it is necessary to supply necessary amounts in proper proportions of selected nutrients such as minerals in the feed media in order to assure proper microorganism growth, and to maximize the assimilation of the oxygenated hydrocarbon by the cells in the microbial conversion process. Phosphorus as phosphate, magnesium, calcium, sodium, manganese, molybdenum, and copper ions appear to provide essential needs. Other medium components, such as trace mineral components, and the like, are well known to those skilled in the art. Other materials called "growth factors", e.g., vitamins and the like, can be added as required for optimum growth of a particular microorganism. Of course, sufficient water is utilized in the fermentation process to provide for the particular requirements for the microorganisms involved.

In the continuous process, air or other oxygen-containing gas, nutrient medium, nitrogen source, and oxygenated hydrocarbon feedstock are fed continuously, generally separately for separate control. The addition rate of the various streams can be varied so as to obtain as rapid a cell growth as possible consistent with the efficient utilization of the oxygenated hydrocarbon input, so that the objective of a maximized high yield of cell weight per weight of carbon and energy source material charged can be obtained. The feed rate of the carbon and energy source material should be adjusted so that the amounts being fed to the fermentor substantially are the same as the rate of consumption by the microorganism, so as to avoid overfeeding, particularly of toxic materials, since a buildup of alcohol, for example, might tend to inhibit the growth or even kill the microorganisms. A satisfactory condition usually is exhibited by there being little or no carbon and energy source material in the effluent being withdrawn from the fermentor, though a satisfactory check can be obtained by watching the carbon and energy source content of the fermentor effluent and maintaining it at a desirable low level for control purposes such as less than about 0.5 volume percent based on liquid content. Relatively high concentrations of the oxygenated hydrocarbon substrate are to be avoided.

Instrumentation can be and preferably is maintained to measure cell densities, pH, dissolved oxygen content, and alcohol or other feedstock concentrations in the fermentation section, temperature, feed rates at input and output streams, cooling water flow and temperature, and the like. It is preferred the materials being fed to the fermentor be sterilized prior to introduction thereinto. My apparatus can be employed as a nonfoam-filled fermentor, though foam-filled operation generally is to be preferred, because this tends to maximize exposure of liquid to oxygen, and also assist in heat transfer. Foam-filled operation is particularly suited for carrying out fermentation processes in which large quantities of gases are maintained in intimate contact with the liquid phase so as to obtain reactions along relatively large areas of contacting interface.

After the fermentation stream is subjected to cell concentration, and a concentrated stream then is produced, the concentrated cells in accordance with my apparatus and process are sent to cell recovery. The cells can be separated from the concentrate by centrifugation, filtration, or the like. The cell-free effluent then can be treated with such as an acetone or a lower alcohol such as methanol to precipitate any extracellular polymeric material contained in this effluent. If desired, the effluent can be treated by solvent extraction and/or base extraction to recover other extracellular products which can include pigments, vitamins, or organic acids coproduced during the culturing process.

The microbial cells themselves generally are killed by heat or chemical means. The protein cells, the SCP, becomes a valuable source of protein for animals and may be, if necessary, further treated to become a valuable source of comestible protein for humans.

The disclosure illustrates the value and effectiveness of my invention.

I claim:

1. A fermentation apparatus for improved oxygen utilization adapted for the continuous aqueous aerobic fermentation of a microorganism, comprising a fermentation section with an upper contiguous absorber section communicating therewith and adapted to the passage of gaseous effluent from the upper area of said fermentation section into the lower portion of said absorber section, wherein said fermentation section is adapted to contain liquid aqueous ferment and comprises means for receiving a molecular oxygen-containing gas positioned in the lower portion of said fermentation section below the normal liquid level of said aqueous liquid ferment, means adapted for receiving a carbon energy source material and a nitrogen source material, means for withdrawing aqueous fermentation liquor rich in cellular material from said fermentation section, means for separating cellular material from said rich aqueous fermentation liquor, leaving lean fermentation liquor, means for cooling said lean fermentation liquor, wherein said absorber section comprises, in sequence relative to said fermentation section, a foam-breaking zone, a gas-contacting zone, a liquid knock-out zone of substantially expanded diameter relative to said gas-contacting zone and sufficient to substantially reduce the linear gas velocity of gases exiting said gas-contacting zone, gas-venting means at the upper area of said knockout zone, means for recycling said cooled lean fermentation liquor to said gas-contacting zone, and means for feeding make-up water and nutrients to said absorber section.

2. The apparatus according to claim 1 further comprising a pH controller-sensor positioned to sense the pH of the aqueous ferment, producing a pH-responsive signal therefrom, and adjusting the feed of said nitrogen source in response to said pH-responsive signal.

3. The apparatus according to claim 1 further comprising a dissolved oxygen sensor positioned to monitor the dissolved oxygen content of said aqueous ferment, producing an oxygen-responsive signal therefrom, and adjusting the feed of said carbon energy source material in response to said oxygen-responsive signal.

4. The fermentation apparatus according to claim 1 wherein said gas-contacting zone comprises a series of sieve trays.

5. The fermentation apparatus according to claim 4 wherein said foam-breaking zone comprises a series of multiple perforated cone baffles.

6. The apparatus according to claim 1 wherein said fermentation section has a ratio of about 2:1 to 6:1 length:diameter;

said gas-contacting zone of said absorber section has a ratio of about 12:1 to 24:1 length:diameter;

said fermentation section has a height:gas-contacting zone height ratio in the range of about 0.6:1 to 1.5:1; and said fermentation section has a diameter of about 3 to 8 times the diameter of said gas-contacting zone.

7. The apparatus according to claim 6 wherein said fermentation section has a ratio of about 2.5:1 to 4.5:1 length: diameter; said gas-contacting zone of said absorber section has a ratio of about 14:1 to 20:1 length:diameter; the ratio of the height of said fermentation section:gas-contacting zone height is in the range of about 0.7:1 to 1.2:1; and said fermentation section has a diameter of about 4 to 6 times the diameter of said gas-contacting zone.

8. The apparatus according to claim 1 wherein said fermentation section is about 5 feet in diameter and about 16 feet high, said gas-contacting zone is about 1 foot in diameter and about 16 feet high, and said foam-breaking zone and liquid knock-out zone are each about 2.5 to 3 feet in height.

9. The apparatus according to claim 1 wherein said liquid knock-out zone is a zone of sufficient diameter to provide about a 50 percent reduction in linear gas velocity from said gas-contacting zone.

10. The apparatus according to claim 1 wherein said means adapted for separating cellular material from said aqueous ferment withdrawn from said fermentation section comprises a cyclone.

* * * * *